US007306578B2

(12) United States Patent
Gray et al.

(10) Patent No.: US 7,306,578 B2
(45) Date of Patent: Dec. 11, 2007

(54) LOADING MECHANISM FOR INFUSION PUMP

(75) Inventors: Larry B. Gray, Merrimack, NH (US); Richard Lanigan, Concord, NH (US)

(73) Assignee: DEKA Products Limited Partnership, Manchester, NH (US)

(*) Notice: Subject to any disclaimer, the term of this patent is extended or adjusted under 35 U.S.C. 154(b) by 0 days.

(21) Appl. No.: 10/037,614

(22) Filed: Jan. 4, 2002

(65) Prior Publication Data

US 2003/0130618 A1 Jul. 10, 2003

(51) Int. Cl.
*A61M 1/00* (2006.01)

(52) U.S. Cl. .................................................. 604/151

(58) Field of Classification Search ................ 604/131, 604/133, 151–155, 208, 209, 211, 228, DIG. 1, 604/224, 110, 187, 207, 232; 128/DIG. 13, 128/DIG. 12
See application file for complete search history.

(56) References Cited

U.S. PATENT DOCUMENTS 4,392,847 A 7/1983 Whitney et al.
4,493,704 A * 1/1985 Beard et al. ................ 604/154
4,648,872 A * 3/1987 Kamen ....................... 604/155
4,834,712 A 5/1989 Quinn et al. ................ 604/175
5,304,152 A * 4/1994 Sams ......................... 604/207
5,342,324 A 8/1994 Tucker ....................... 604/264
5,417,667 A 5/1995 Tennican et al. ............ 604/191
5,507,727 A 4/1996 Crainich
5,522,803 A 6/1996 Teissen-Simony .......... 604/177
5,533,996 A 7/1996 Murphey et al. ........... 604/283
5,545,143 A 8/1996 Fischell et al. ............. 604/180
5,545,152 A 8/1996 Funderburk et al. ........ 604/283
5,558,641 A 9/1996 Glantz et al. ................. 604/93
5,562,618 A 10/1996 Cai et al. ...................... 604/93
5,569,026 A 10/1996 Novak ..................... 417/477.1
5,584,813 A 12/1996 Livingston et al. ......... 604/177
5,647,854 A 7/1997 Olsen et al. ................ 604/174
5,762,632 A 6/1998 Whisson ..................... 604/171
5,776,116 A 7/1998 Lopez et al. ................ 604/283
5,810,001 A 9/1998 Genga et al. .......... 128/202.27
5,843,146 A 12/1998 Cross, Jr. .................... 607/115
5,954,697 A * 9/1999 Srisathapat et al. ......... 604/155
5,968,011 A 10/1999 Larsen et al. ................. 604/93
5,980,506 A 11/1999 Mathiasen .................. 604/535

(Continued)

FOREIGN PATENT DOCUMENTS

EP 0 398 394 11/1984

(Continued)

OTHER PUBLICATIONS

International Search Report for corresponding European patent application (BP).

*Primary Examiner*—Nicholas D. Lucchesi
*Assistant Examiner*—Matthew F. DeSanto
(74) *Attorney, Agent, or Firm*—Bromberg & Sunstein LLP

(57) ABSTRACT

A loading mechanism for a medication infusion pump. The mechanism includes a medication reservoir, a plunger, a threaded plunger rod offset from the axis of the reservoir and an infusion pump with a drive screw that is offset from the axis of a pump barrel. The pump barrel receives the assembly comprising the reservoir, plunger and plunger rod.

10 Claims, 8 Drawing Sheets

U.S. PATENT DOCUMENTS

| | | | | |
|---|---|---|---|---|
| 6,017,326 | A | 1/2000 | Pasqualucci et al. | 604/153 |
| 6,017,328 | A | 1/2000 | Fischell et al. | 604/180 |
| 6,042,565 | A | 3/2000 | Hirschman et al. | |
| 6,056,718 | A | 5/2000 | Funderburk et al. | 604/93 |
| 6,063,059 | A * | 5/2000 | Kriesel | 604/133 |
| 6,086,575 | A | 7/2000 | Mejslov | 604/533 |
| 6,096,011 | A | 8/2000 | Trombley, III et al. | 604/256 |
| 6,099,507 | A | 8/2000 | Heinzerling | 604/174 |
| 6,123,690 | A | 9/2000 | Mejslov | 604/283 |
| 6,248,093 | B1 * | 6/2001 | Moberg | 604/131 |
| 6,645,177 | B1 * | 11/2003 | Shearn | 604/155 |
| 2004/0158207 | A1 | 8/2004 | Hunn et al. | 604/164.01 |

FOREIGN PATENT DOCUMENTS

| | | | |
|---|---|---|---|
| EP | 0 256 694 | A1 | 2/1988 |
| EP | 0 258 566 | A2 | 3/1988 |
| EP | 0 749 757 | A2 | 1/1992 |
| WO | WO 99/44655 | | 9/1999 |
| WO | WO 02/053220 | A2 | 7/2002 |

* cited by examiner

LOADING MECHANISM FOR INFUSION PUMP

TECHNICAL FIELD AND BACKGROUND ART

The present invention relates to medical infusion pumps and more particularly to improved devices for loading medication reservoirs.

Medical infusion pumps have been advantageously employed, for example, to simulate the action of the human pancreas, providing a continuous delivery of insulin to patients with diabetes. These pumps typically include a microprocessor controlled syringe pump, an insulin filled syringe, a hub and tubing set and a cannula. The pump is often worn in a carrying case on the patient's belt or in other locations such as a pocket. The syringe is mounted in the syringe pump and can contain enough insulin for several days. The hub connects the syringe to the tubing set. The cannula is at the end of the tubing set and can be either steel or softer teflon. The cannula is inserted into fatty tissue and the insulin is injected subcutaneously.

Prior art infusion pumps have been cumbersome to load, requiring a series of steps that often require the user to carefully align components of a pump drive assembly with the syringe.

SUMMARY OF THE INVENTION

In a first embodiment of the invention there is provided a drive assembly for an infusion pump. The drive assembly includes a pump barrel that has a clearance hole for receiving and guiding a threaded plunger rod. A threaded, rotating drive screw is provided whose longitudinal axis is parallel to and offset from the pump barrel axis. The plunger rod engages and disengages the drive screw when the pump barrel is rotated, thereby rotating the rod about the longitudinal axis of the barrel. This embodiment of the invention may be used, for example, in devices for injecting medication and delivering other fluid materials such as caulk, cement, grease, etc.

In another embodiment of the invention, the drive assembly of the first embodiment further comprises a variable volume reservoir including a plunger. The plunger is connected to the plunger rod, which rod varies the volume of the reservoir as the plunger is displaced. A locking hub is provided that connects to the top of the reservoir. The locking hub contacts the pump barrel, rotating the barrel and forcing the rod into and out of engagement with the drive screw. The reservoir is loaded into the pump by aligning the plunger rod with the hub, inserting the reservoir into the pump barrel with the plunger rod guided by the clearance hole, and rotating the hub to lock the reservoir into the pump.

In a further embodiment of the invention, the drive screw threads and the rod threads of the first embodiment are buttress threads.

In another embodiment of the invention, the pump barrel of the first embodiment has a locking tab to inhibit rotation of the barrel about the longitudinal barrel axis.

In a further embodiment of the invention, a variable volume reservoir is provided together with a plunger connected to the bottom of the reservoir. A threaded plunger rod is also provided that is connected to the plunger, such that the plunger rod is parallel to and offset from the longitudinal axis of the reservoir. The plunger rod is capable of mating with a threaded drive screw whose axis is offset from and parallel to the longitudinal axis of the reservoir. The plunger rod, when axially displaced, causes a change in volume of the reservoir. This embodiment of the invention can be used in combination with a drive assembly to deliver a fluid.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Embodiments of the present invention advantageously address simplifying the loading of medication reservoirs in an infusion pump.

Figure 1:
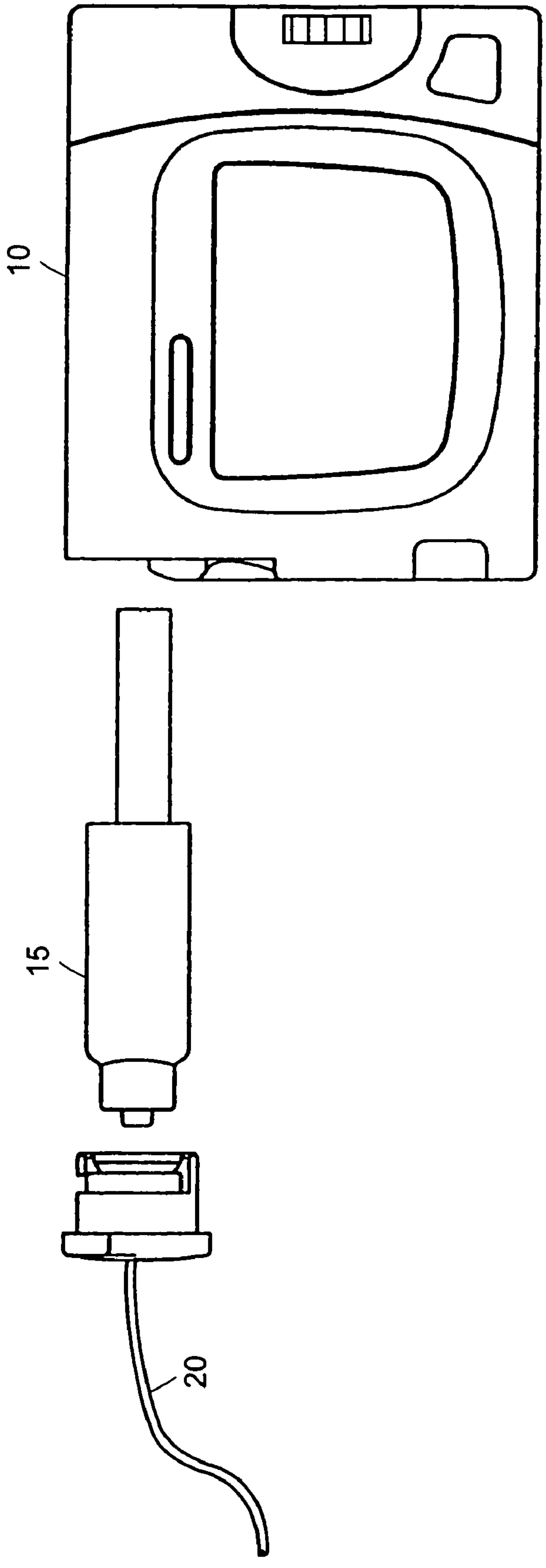
FIG. 1 is a top-level view of an infusion pump according to an embodiment of the invention.

FIG. 1 is an overall view of an infusion pump according to an embodiment of the present invention. A pump assembly 10 contains the components needed to cause a reservoir assembly 15 to deliver medication to a user. The reservoir assembly 15 may contain enough medication, such as insulin, for several days for a typical user. A tubing set 20, connected to the reservoir assembly, contains the cannula through which the medication is delivered to the user.

Figure 2:
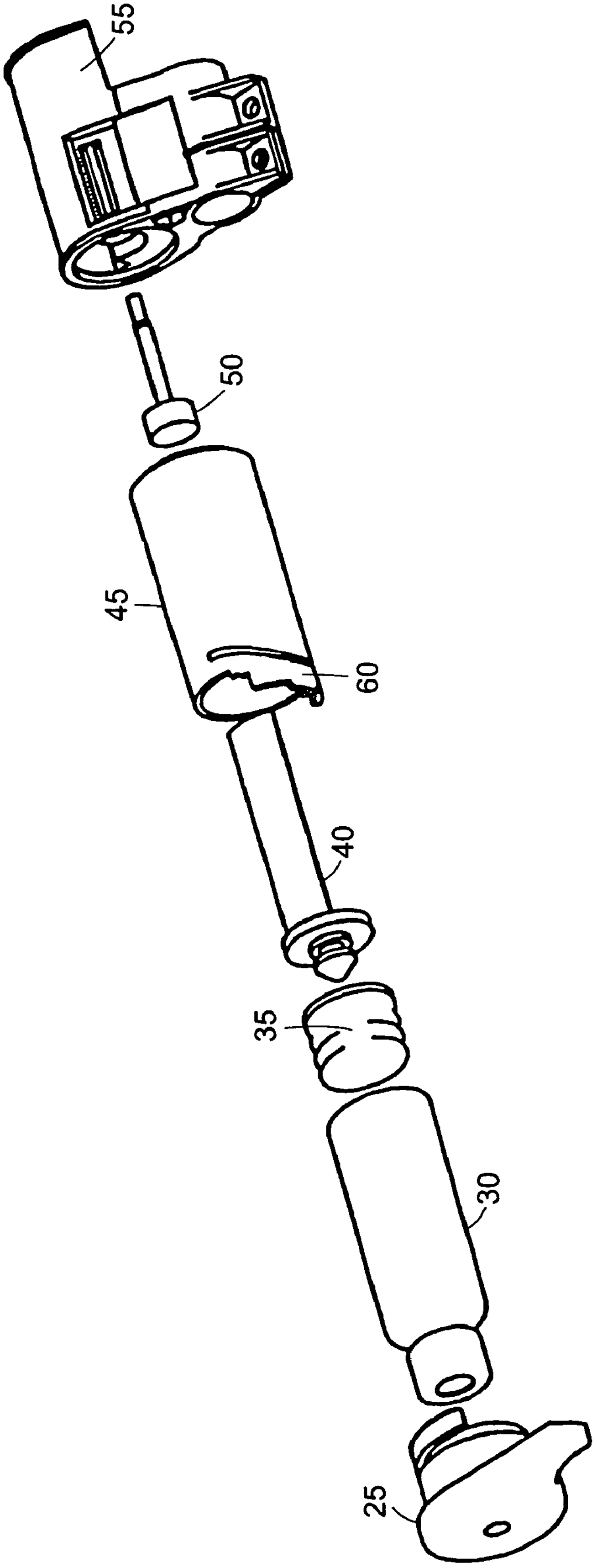
FIG. 2 is an exploded view of a drive mechanism for the infusion pump of FIG. 1.

FIG. 2 shows an exploded view of the drive mechanism of the infusion pump. A reservoir assembly 15 comprises a reservoir 30, plunger 35 and plunger rod 40. The reservoir 30 contains the medication for delivery to the user and is of variable interior volume. The interior volume is the liquid capacity of the reservoir. The plunger 35, inserted into the bottom of the reservoir, causes the volume of the reservoir to change as the plunger is displaced along the longitudinal axis of the reservoir. The plunger rod 40 is connected to the plunger with the rod's longitudinal axis displaced from and parallel to the longitudinal axis of the reservoir. The plunger rod 40 is threaded for at least a portion of the rod's length. A cylindrical pump barrel 45 receives the reservoir assembly 15. The pump barrel constrains the plunger rod, orienting the rod along the longitudinal axis of the barrel. The pump barrel 45 is contained in the pump assembly and may contain a locking tab to prevent rotation of the pump barrel with respect to the assembly. A gear box 55 in the pump assembly 15 includes a drive screw 50 along with motor and gears to turn the drive screw. The drive screw 50 is threaded and the screw's longitudinal axis is aligned parallel to and displaced from the longitudinal axis of the pump barrel. A locking hub 25 is attached to the top of the reservoir.

Figure 3:
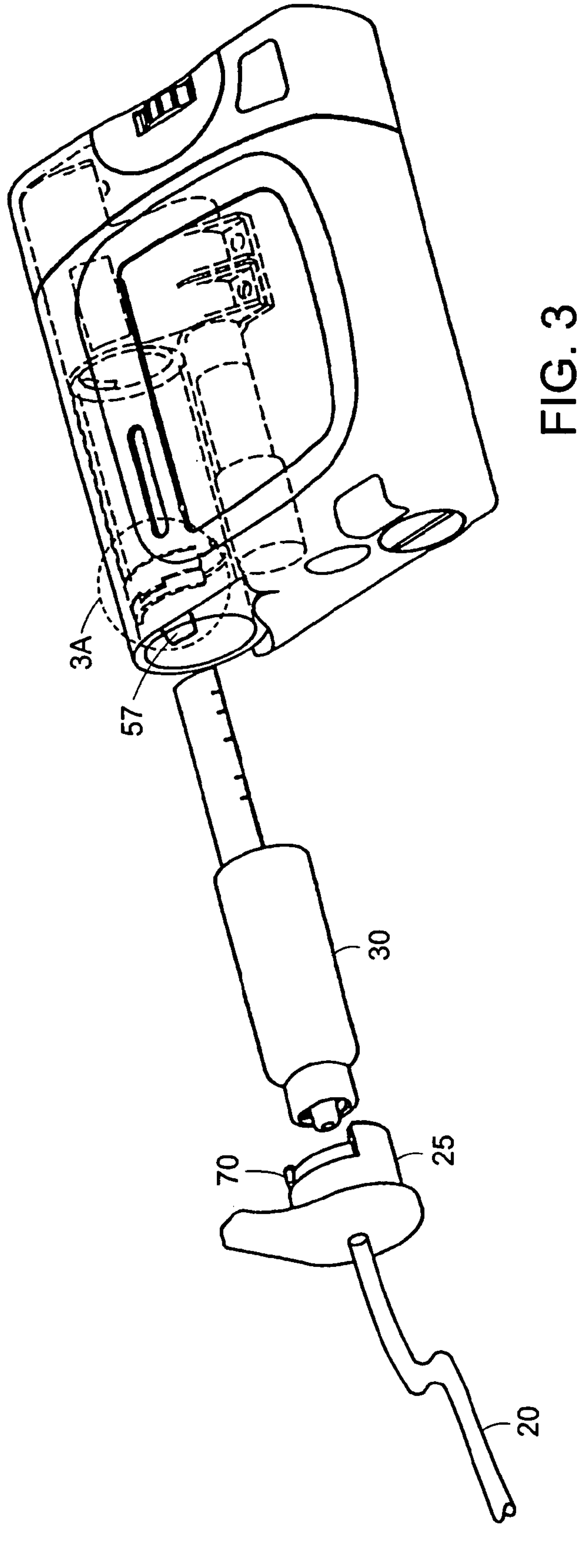
FIG. 3 is shows an embodiment of a pump barrel locking mechanism.
Figure 3A:
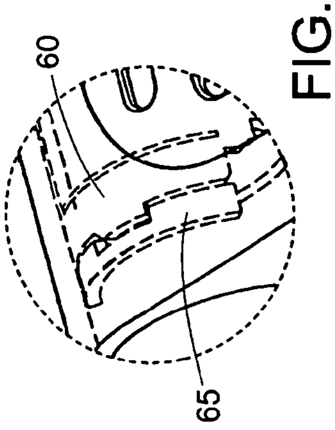

FIG. 3 shows a pump barrel locking mechanism for an embodiment of the invention. The pump barrel 45 includes a clearance hole 72 in one end (shown in FIG. 4) that guides the plunger rod 40 during insertion of the reservoir assembly 15 into the barrel. To ensure that the drive screw 50 does not interfere with the plunger rod 40 during insertion of the reservoir assembly, the pump barrel 45 maintains a fixed position relative to the pump assembly 10. The position of the pump barrel relative to the pump assembly may be maintained, for example, by a locking tab 60 included in the pump barrel that engages a pump barrel stop 65 in the pump assembly 10. The hub 25 may include a flange 70 which dislodges the locking tab 60 from the barrel stop 65 when the hub turns, allowing the hub to rotate the pump barrel 45.

Figure 4B:
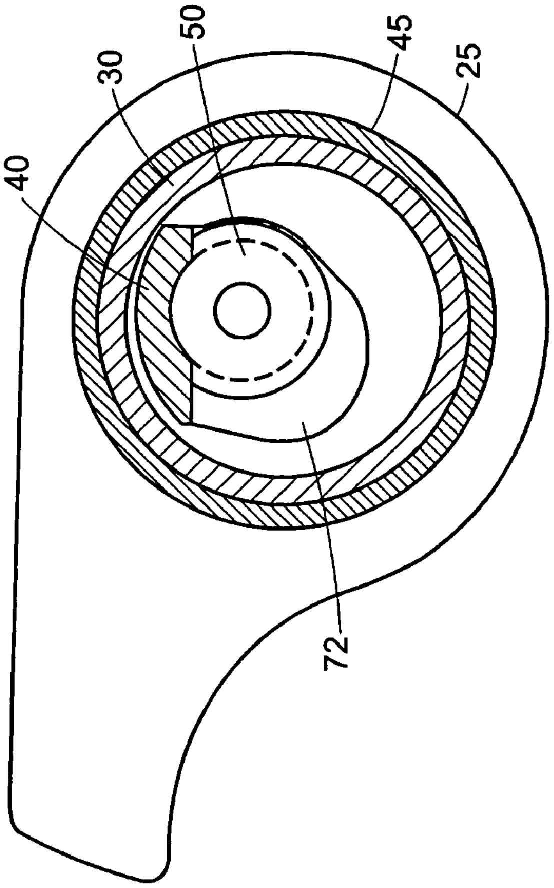
FIG. 4 shows the relation of the drive screw to the plunger rod for the infusion pump of FIG. 1.
Figure 4A:
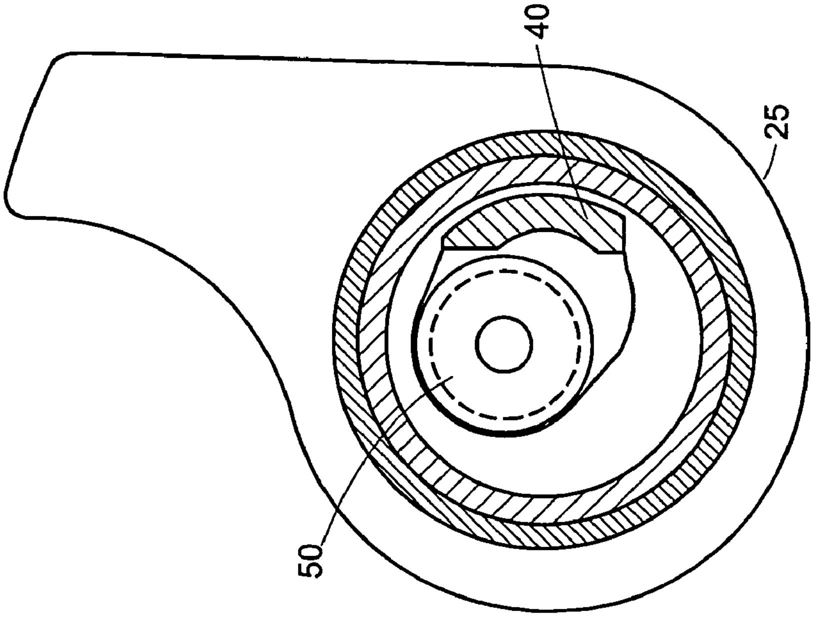

FIGS. 4A and 4B are views along the longitudinal axis of the pump barrel 45 showing the relation of the drive screw to the plunger rod in a loading position and in an engaged position, respectively. The reservoir assembly 15 is positioned for loading so that the plunger rod 40 does not contact the drive screw 50, as shown in FIG. 4A. With the pump barrel positioned appropriately with respect to the pump assembly, the plunger rod clearance from the drive screw is determined by the placement of the clearance hole 72 in the pump barrel base, which hole receives and guides the plunger rod. The clearance hole may be tapered to ease insertion of the rod. The drive screw 50 fits in a clearance hole 72 in the pump barrel 45. Once the reservoir assembly 15 is inserted into the pump assembly 10, the barrel 45 is rotated by the locking hub, causing the plunger rod 40 to turn and to engage the drive screw 50, as shown in FIG. 4B. This embodiment advantageously simplifies reservoir loading.

In a specific embodiment of the invention, the plunger rod threads and the drive screw threads are buttress threads. This embodiment advantageously addresses eliminating reaction forces on the plunger rod normal to the direction of the rod's longitudinal axis. Such reaction forces may cause the rod to deflect and skip a thread on the drive screw, resulting in under delivery of medication to the user. Buttress threads eliminate the normal component of the reaction force.

Figure 5:
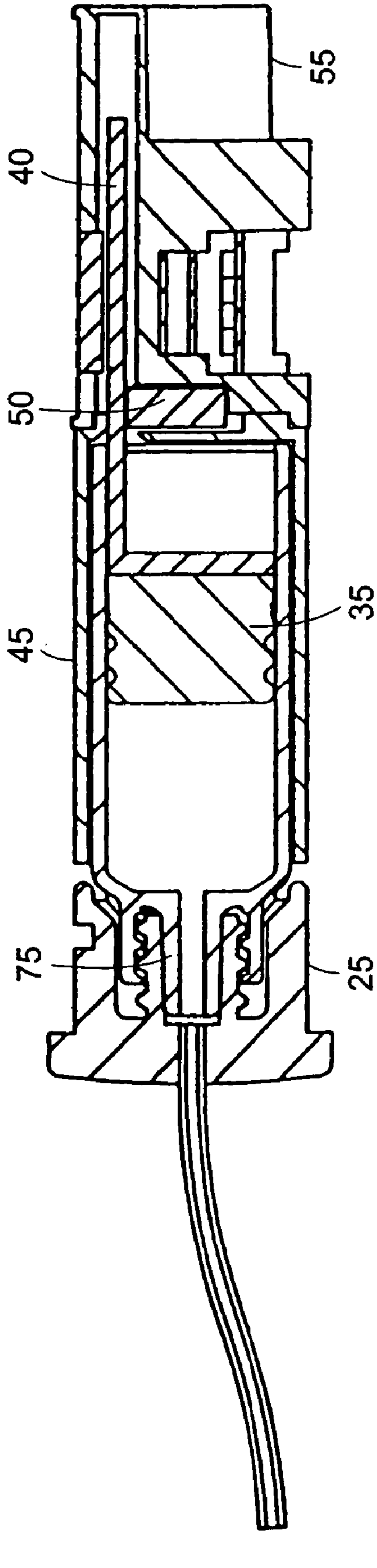
FIG. 5 shows a connection from a reservoir to a tubing set.

In an embodiment of the present invention, the locking hub 25 may be connected to the reservoir 30 by a tapered luer connection, as shown in FIG. 5. The reservoir has a male luer taper integrally molded into the reservoir's top. Surrounding the male luer is an annulus with an internal female thread. Similarly, the hub 25 contains the mating female luer and threaded male connection.

Figure 6:
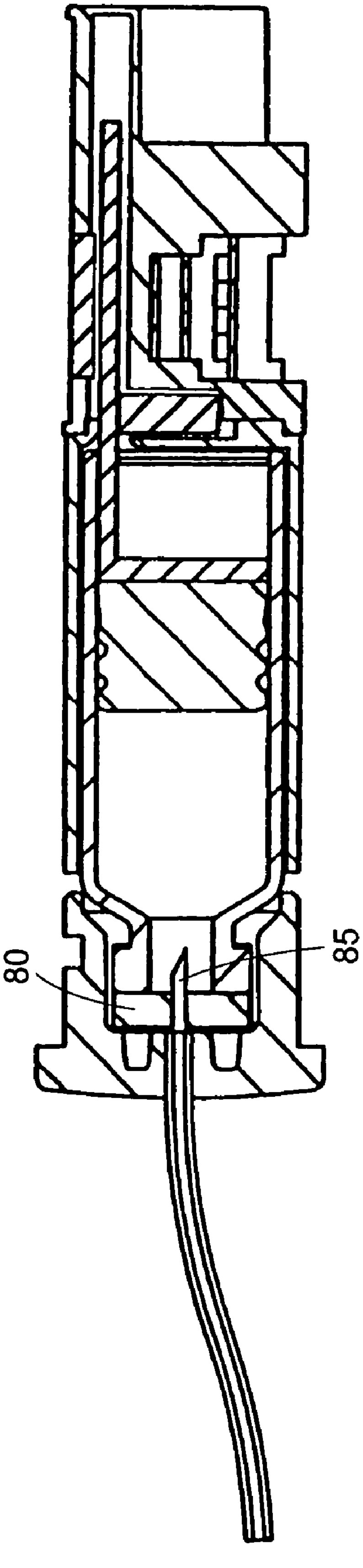
FIG. 6 illustrates another method of connecting a reservoir to a tubing set.

In another embodiment of the invention, a needle connection is provided between reservoir 30 and hub 25. As shown in FIG. 6, the reservoir includes a rubber septum 80 that is attached to the reservoir with a crimped metal collar. A needle 85, integral to the hub, pierces the septum and fluid can then flow from the reservoir to the tubing set.

Figure 7:
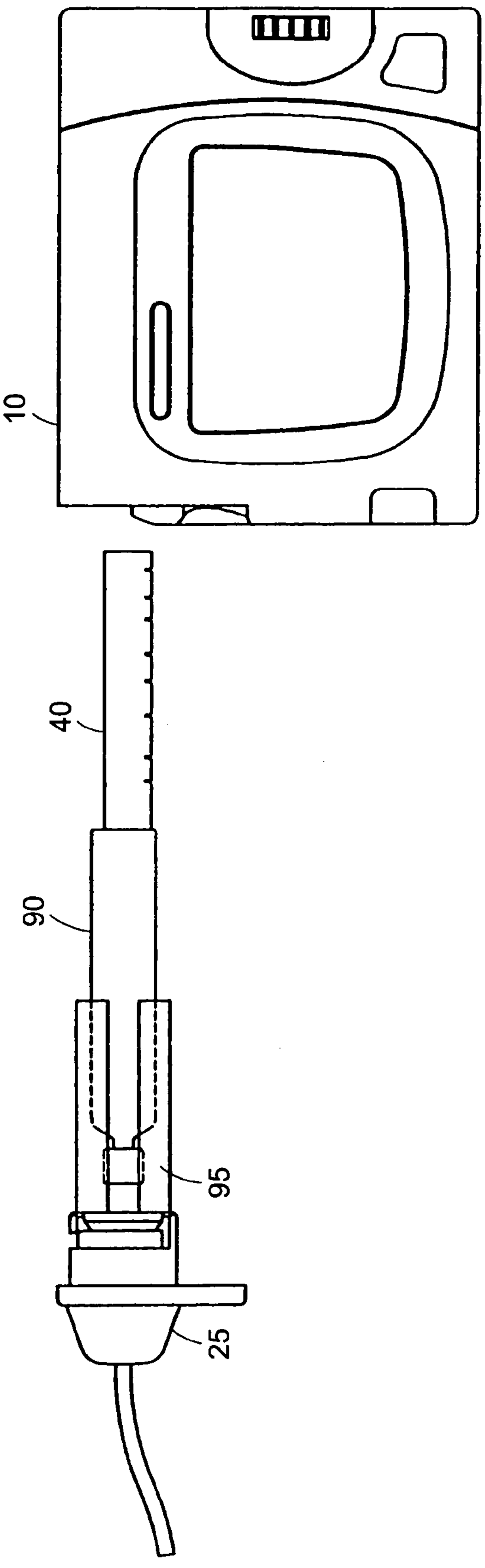
FIG. 7 shows an adapter for using a small diameter reservoir with the pump assembly according to another embodiment of the invention.
Figure 8B:
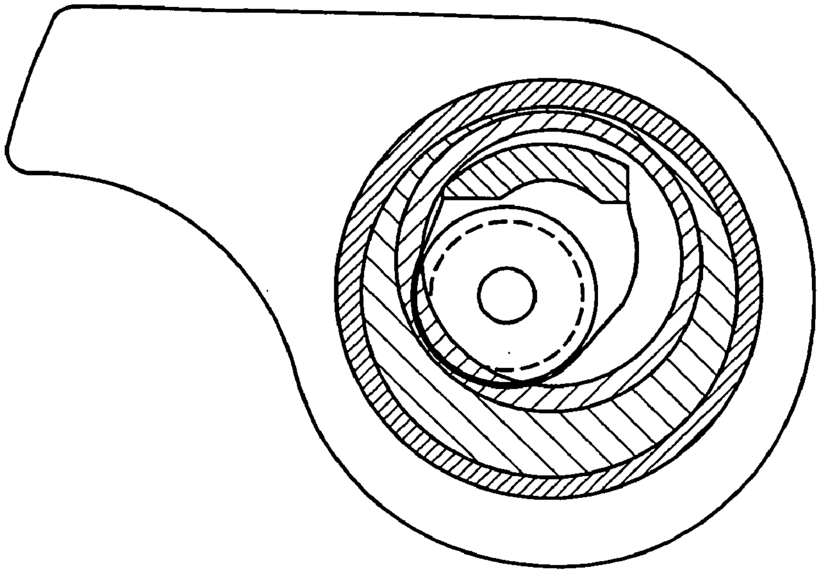
FIG. 8 is an on-axis view of the adapter of FIG. 7.
Figure 8A:
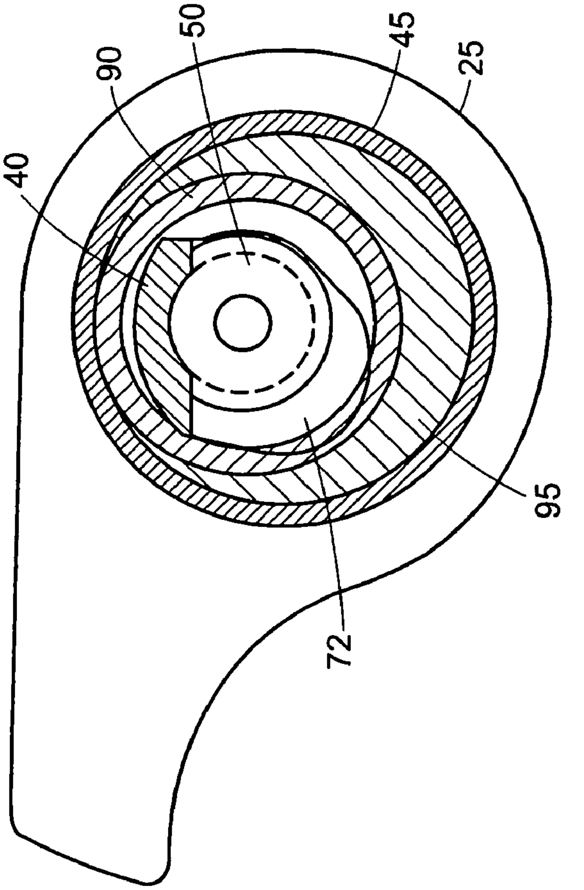

In a further embodiment of the invention, as shown in FIG. 7, an adapter 95 is provided to permit a reservoir 90 whose diameter is substantially smaller than the diameter of the pump barrel 45 to be used with the pump assembly 10. The adapter 90 may be a separate component or may be integrated into the locking hub 25. The adapter 95 aligns and offsets the reservoir's 90 axis parallel to the longitudinal axis of the pump barrel so that the plunger rod 40, when rotated, mates with the drive screw. FIG. 8 shows an on-axis view of the small diameter reservoir 90 when placed in the adapter 95. As will be apparent, the offset provided by the adapter allows the plunger rod 40, when mated with the plunger 35 and reservoir 90, to engage the drive screw 50 in the same fashion as for the first embodiment, described above.

Having described various illustrative embodiments of the present invention, some of its advantages and optional features, it will be apparent that such embodiments are presented by way of example only and not by way of limitation. Those skilled in the art could readily devise alterations and improvements on these embodiments, as well as additional embodiments, without departing from the spirit and scope of the invention. All such modifications are within the scope of the invention as claimed.

What is claimed is:

1. A drive assembly for an infusion pump, the assembly comprising:

a. a reservoir for containing a fluid, the reservoir being the exclusive component of the drive assembly capable of containing a fluid for infusion;

b. a barrel, distinct from the reservoir, for holding the reservoir, the barrel characterized by a longitudinal barrel axis of rotation and a clearance hole in a barrel end;

c. a rotating drive screw, the drive screw having a longitudinal screw axis and exterior threads, the screw axis displaced from and parallel to the barrel axis; and d. a plunger rod, the rod having threads at least part of its length, the rod inserted through the clearance hole, the rod threads interlocking with and disengaging from the screw threads by rotating the barrel about the barrel axis.

2. A drive assembly according to claim 1, wherein the reservoir includes a plunger in engagement with the plunger rod, the plunger when axially displaced causing a change in volume in the reservoir; the drive assembly further including a locking hub, the hub in mechanical connection with the reservoir and the barrel, the hub capable of rotating the barrel, forcing the rod threads into and out of mechanical engagement with the drive screw threads.

3. A drive assembly according to claim 2 wherein the barrel further includes a locking tab to inhibit rotation of the barrel about the barrel axis and the locking hub includes a flange, the flange for dislodging the locking tab allowing the barrel to rotate.

4. A drive assembly according to claim 2 wherein the locking hub further includes an adapter, the adapter for receiving the reservoir, the adapter providing an axial offset to the reservoir so that the plunger rod threads can engage with the drive screw threads.

5. A drive assembly according to claim 1 wherein the drive screw threads and the rod threads are buttress threads.

6. A drive assembly according to claim 1 wherein the barrel further includes a locking tab to inhibit rotation of the barrel about the barrel axis.

7. A drive assembly for an infusion pump, the assembly comprising:

a fluid reservoir containing a fluid for delivery by the pump;

a pump barrel having a longitudinal barrel axis and holding the fluid reservoir;

a plunger rod having a single longitudinal rod axis parallel to and displaced from the longitudinal barrel axis and threaded along at least a portion of its length, the plunger rod terminating in a plunger at one end of the single longitudinal rod axis, the plunger being inserted into one end of the fluid reservoir so as to change the volume of the reservoir as the plunger is displaced within the reservoir; and a threaded drive screw having a longitudinal screw axis parallel to and displaced from the single longitudinal rod axis;

the assembly being characterized by:

(i) a loading position in which the plunger rod threads and the drive screw threads are not engaged so as to facilitate loading fluid into the fluid reservoir, and (ii) an operating position in which the plunger rod threads and the drive screw threads are engaged such that rotation of the drive screw displaces the plunger to change the volume of the reservoir to deliver fluid out from the reservoir.

8. A drive assembly according to claim 7, wherein rotation between the plunger rod and the drive screw engages and disengages them to switch from one operating position to another.

9. A drive assembly according to claim 7, further comprising:

a locking hub for controlling the engaging and disengaging of the plunger rod threads and the drive screw threads.

10. A drive assembly according to claim 7, wherein the plunger rod threads and the drive screw threads are buttress threads.

* * * * *